United States Patent [19]

Okamoto

[11] Patent Number: 5,580,730
[45] Date of Patent: Dec. 3, 1996

[54] ENZYME DIGESTION METHOD FOR THE DETECTION OF AMPLIFIED DNA

[75] Inventor: Naoaki Okamoto, South Setauket, N.Y.

[73] Assignee: Olympus America, Inc., Lake Success, N.Y.

[21] Appl. No.: 293,638

[22] Filed: Aug. 19, 1994

[51] Int. Cl.[6] .......................... C07H 21/04; C12P 19/34; C12Q 1/68
[52] U.S. Cl. .................................. 435/6; 435/15; 435/18; 435/91.1; 435/91.2; 536/24.33; 536/26.6; 935/77; 935/78
[58] Field of Search .............................. 435/6, 91.1, 91.2, 435/15, 18; 536/26.6, 24.33; 935/77, 78

[56] References Cited

U.S. PATENT DOCUMENTS

| 5,035,996 | 7/1991 | Hartley | 435/6 |
| 5,210,015 | 5/1993 | Gelfand et al. | 435/6 |
| 5,333,675 | 8/1994 | Mullis et al. | 165/12 |

OTHER PUBLICATIONS

Saiki R. K., Scharf S., Faloona F., Mullis K. B., Horn G. T., Erlich H. A., and Arnheim. Enzymatic Amplification of β–Globin Genomic Sequences and Restriction Site etc.(1985) Science 230, 1350–1354.

Saiki R. K., Gelfand D. H., Stoffel S., Scharf S. J., Higuchi R., Horn G. T., Mullis K. B., and Erlich H. A. Primer–Directed Enzmatic Amplification of DNA With A Thermostable DNA Polymerase (1988) Science 239, 487–489.

Maeda M., Murayama N., Ishii N., Uryu N., Ota M., Tsuji K., and Inoko H. A simple and rapid method for HLA–DQA1 genotyping by digestion of PCR–amplified DNA with allele specific restriction endonucleases (1989) Tissue Antigens 34, 290–298.

Uryu N., Maeda M., Ota M., Tsuji K., and Inoko H. A simple and rapid method for HLA–DRB and –DQB typing by digestion of PCR–amplified DNA with allele specific restriction endonucleases (1990) Tissue Antigens 35, 20–31.

Angelini G., de Preval C., Gorski J., and Mach B, High-resolution analysis of the human HLA–DR polymorphism by hybridization with sequence–specific oligonucleotide probes, Immunology(1986) Proc. Nat'l. Acad. Sci. USA. 83, 4489–4493.

Bugawan T. L., Saiki R. K., Levenson C. H., Watson R. M., and Erlich H. A. The Use of Non–Radioactive Oligonucleotide Probes To Analyze Enzymaticaly Amplified DNA For Prenatal Diagnosis And Forensic HLA Typing, (Aug. 1988) Biotechnology 6, 943–947.

Tiercy J. M., Jeannet M., and Mach B. A New Approach For The Analysis Of HLA Class II Polymorphism: HLA Oligo-typing, (1990) Blood Review 4, 9–15.

Eliaou J. F., Humbert M., Balaguer P., Gebuhrer L., Amsellem S., Betuel H., Nicolas J. C., and Clot J. Amethod of HLA class II typing using on–radioactive labelled oligonucleotides (1989) Tissue Antigens 33, 475–485.

Schaf S. J., Grmith R. L., and Erlich H. A., Rapid Typing of DNA Sequence Polymorphism etc., (1991) Hum. Immunol. 30, 190–201.

(List continued on next page.)

*Primary Examiner*—W. Gary Jones
*Assistant Examiner*—Paul B. Tran
*Attorney, Agent, or Firm*—Kenyon & Kenyon

[57] ABSTRACT

Qualitative and quantitative methods for detecting the presence of double-stranded, non-5'-phosphorylated DNA in samples that may also contain 5'-phosphorylated DNA and/or single-stranded DNA are described. These methods involve treating the sample with an enzyme that specifically degrades 5'-phosphorylated DNA together with an enzyme that specifically degrades single-stranded DNA. More specifically, methods are described for the detection of the products of DNA amplification reactions, such as the polymerase chain reaction (PCR), wherein post-amplification enzyme digestion substantially reduces or eliminates background signals that are apparently caused by the presence of template DNA and primers in the sample after amplification is complete.

16 Claims, 8 Drawing Sheets

OTHER PUBLICATIONS

Kawai S., Maekawajiri S., and Yamane A. A Simple Method of Detecting Amplified DNA With Immobilized Probes on Microtiter Wells, (1993) Anal. Biochemistry 209, 63–69.

Lazaro A. M., Fernandez–Vina M. A., Liu Z., and Stastny P., Enzyme–Linked DNA Oligotyping A Practical Method For Clinical HLA–DNA Typing, (1993) Hum. Immunol. 36, 243–248.

Nevinny–Stickel C. and Albert E. D., HLA Class II Typing In A Microtitre Plate Formate Using Digoxigenin–Labelled Amplified DNA etc., (1993) Eur. J. Immunogenet. 20, 419–427.

Saiki R. K., Walsh P. S., Levenson C. H., and Erlich H. A., Genetic Analysis of Amplified DNA with Immobilized Sequence–Specific Oligonucleotide Probes, (1989) Proc. Nat'l. Acad. Sci. USA 86, 6230–6234.

Erlich H., Bugawan T., Begovich A. B., Scharf S., Griffith R., Saiki R., Higuchi R., and Walsh P. S. HLA–DR, DQ and DP Typing Using PCR Amplification And Immobilized Probes, (1991) Eur. J. Immunogenet 18, 33–55.

Caillat–Zucman S., Garchon H–J, Constantino F., Cot S., and Bach J–F., Automation of Large–Scale HLA Oligotyping Using A Robotic Workstation, (1993) Biotechniques 15, 526–531.

Fugger L., Morling N., Ryder L. P., Odum N., and Svejgaard A., Technical aspects of typing for HLA–DP alleles using allele–specific DNA in vitro amplification and sequence–specific oligonucleotide probes, (1990) J. Immunol Method. 129, 175–185.

Olerup O., and Zetterquist H., HLA–DRB1*01 subtyping by allele–specific PCR amplification: A sensitive, specific and rapid technique, (1991) Tissue Antigens 37, 197–204.

Olerup O., and Zetterquist H., HLA–DR typing by PCR Amplification with Sequence–specific primers (PCR–SSP) etc. (1992) Tissue Antigens 39, 225–235.

Ferencik S. and Grosse–Wilde H., A Simple Photometric Detection Method For HLA–DRB1 Specific PCR–SSP Products, (1993) Eur. J. Immunogenet. 20 123–125.

Chia D., Terasaki P., Chan H., Tonai R. and Siauw P. A., Direct Detection of PCR Products For HLA Class II Typing, (1993) Tissue Antigens 42 146–149.

Higuchi R., Dollinger G., Walsh P. S., and Griffith R., Simultaneous Amplificaiton and Detection of Specific DNA Sequences, (1992) Bio/Technology 10, 413–417.

Higuchi R., Fockler C., Dollinger G., and Watson R., Kinetic PCR Analysis: Real–time Monitoring of DNA Amplification Reactions, (1993) Bio/Techniques 11, 1026–1030.

Glazer A. N., and Rye H. S., Stable dye–DNA intercalation complexes as reagents for high–sensitivity fluorescence detection, (1992) Nature 359, 859–861.

Rye H. S., Dabora J. M., Quesada M. A., Mathies R. A., and Glazer A. N., Fluorometric Assay Using Dimetric Dyes For Double–and Single–Stranded DNA and RNA with Picogram Sensitivity, (1993) Anal. Biochemistry 208, 144–150.

Yang S. Y., Milford E., Hammerling V., and Dupont B., (1989) in Immunobiology of HLA vol. 1. Histocompatibility Testing. The B cell panel designated for the 10th International Histocompatibility Workshop. pp. 11–18 SpringerVerlag, New York.

Hopkins K. A., (1990) ASHI Laboratory Manual. Am. Soc. Histocompatibility Immunogenetics 195–201.

Little J. W., Lehman L. R. and Kaiser A. D. (1967) J. Biol. Chem. 242, 672.

Kwok S. Y., Mack D. H., Mullis K. B., Poiesz B. J., Ehrlich G. D., Blair D. and Friedman–Kein A. S.and Sninsky, J. J., Identification of Human Immunodeficiency Virus Sequences By Using In Vitro Enzymatic Amplification and Oligomer Cleavage Detection, (1987) J Viol. 61, 1690–1694.

Okamoto N., Lee A., Kano T. and Lee T. D. (1994) Homogeneous Fluorescence Detection Method for Human Leukocyte Antigen–DR Typing Following Polymerase Chain Reaction Amplification with Sequence–Specific Primer, Analytical Biochemistry 221, 340–347.

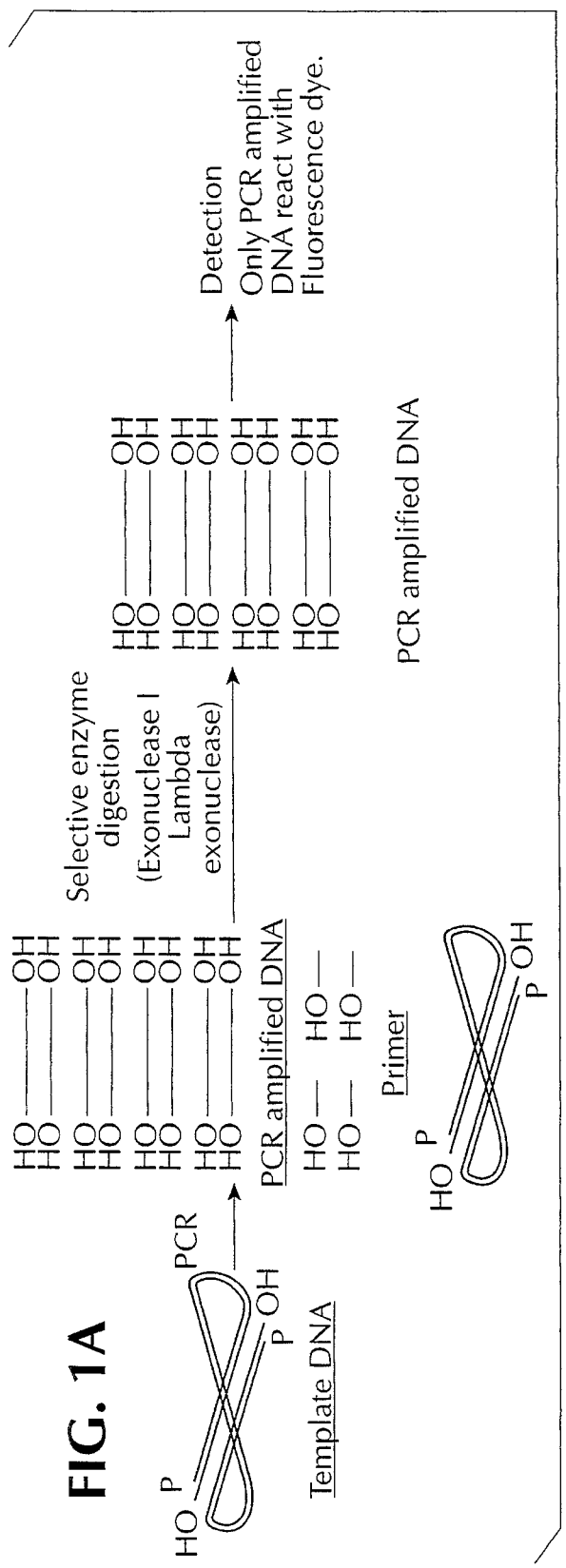
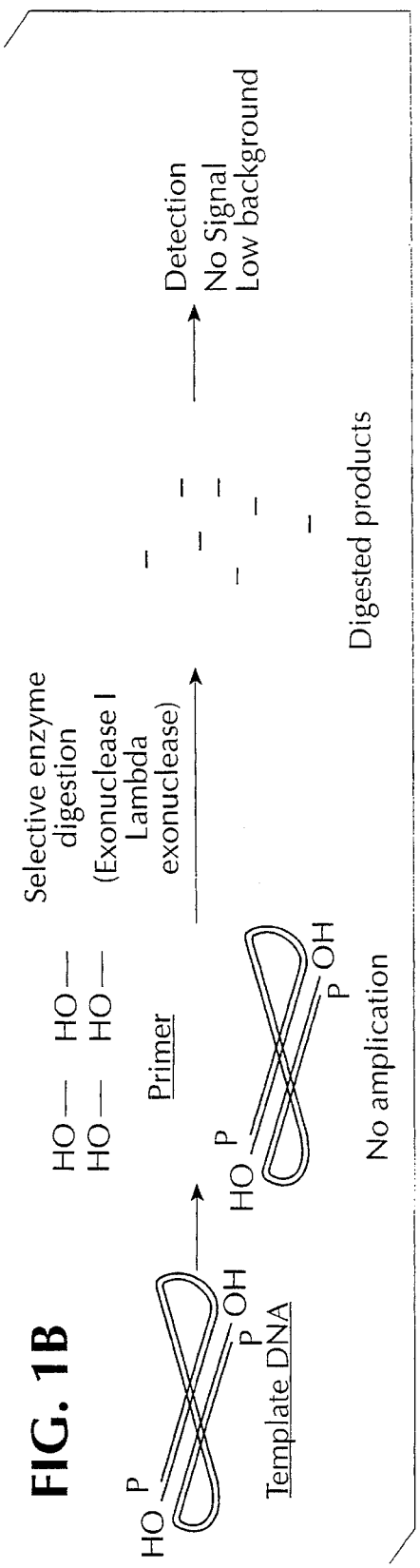

5,580,730

ENZYME DIGESTION METHOD FOR THE DETECTION OF AMPLIFIED DNA

FIELD OF THE INVENTION

The present invention relates to qualitative and quantitative methods for detecting the products of DNA amplification reactions, such as the polymerase chain reaction (PCR). More specifically, the present invention relates to the post-amplification use of an enzyme that specifically degrades phosphorylated DNA together with an enzyme that specifically degrades single-stranded DNA. Such treatment serves to digest DNA other than that produced by amplification, such that methods that detect DNA in the remaining sample will yield qualitative and/or quantitative results that substantially correlate with the presence and relative quantity of amplified product present in said sample. More generally, the present invention relates to the detection of double-stranded, non-5'-phosphorylated DNA in samples that may also contain 5'-phosphorylated DNA and/or single-stranded DNA.

BACKGROUND OF THE INVENTION

It is often desirable to detect certain known or suspected target sequences within samples of DNA that may be derived from biological sources (either directly, or by indirect methods, e.g., reverse transcription of DNA), or which may be derived by artificial means, e.g., chemical synthesis or site-directed mutagenesis. Detection of such target sequences may have utility in determining the presence of infectious diseases such as HIV-I or Hepatitis B virus, as well as in the detection of whether individuals carry genes for genetic diseases such as sickle cell anemia or hemophilia. Such methods may also be useful in identifying whether target sequences are contained in populations of DNA produced by genetic manipulations in vitro.

Perhaps the most powerful methods for detecting such target DNA sequences take advantage of existing and emerging methods for amplifying DNA sequences that may be present in samples in only trace quantities. One particularly well-known amplification method is the polymerase chain reaction (PCR). Once amplified, target DNA sequences can be detected by a variety of methods for the detection of specific DNA sequences, e.g., by gel electrophoresis or by hybridization with labeled probes, or, if the amplified product is present in substantially large quantities in relationship to the DNA present in the original sample, by more simple methods that detect the relative presence of DNA, e.g., by staining with ethidium bromide, which becomes fluorescent upon intercalation between nucleotide bases in double-stranded DNA.

Unfortunately, available methods for detecting DNA amplification products have limitations that diminish the usefulness of such methods for identifying target sequences. For example, gel electrophoresis requires a considerable amount of sample handling, and is thus not suitable for the rapid and cost-effective screening of large numbers of samples. This handling can also lead to false positives if even extremely small amounts of DNA are carried over from sample to sample, as these may become subsequently amplified.

A sense of the importance of such detection methods and the limitations of those currently available can be readily appreciated in the case of methods used to detect the presence of specific HLA-class II molecules. These molecules are highly polymorphic antigens which play a key role in the control of the immune response. For example, the HLA-class II molecules DR and DQ are involved in causing tissue rejection after tissue transplantation, auto-immune diseases, and other immune-mediated disorders. There is therefore a clinical need to be able to detect the presence of these antigens in given individuals, in order to allow for tissue type matching in anticipation of organ transplantation, investigations into auto-immune and other HLA-related diseases, and studies designed to explore the evolution and descendance of these antigens.

Since the development of PCR (1,2), many amplification-dependant approaches have been applied to HLA typing. For example, restriction endonuclease digestion to produce PCR restriction fragment length polymorphism (PCR-RFLP) has been used (3,4), and an even more popular approach has been the hybridization of PCR amplified products with sequence-specific oligonucleotide probes (PCR-SSO) to distinguish between HLA alleles (5–7). Hybridization and detection methods for PCR-SSO typing include the use of non-radioactive labeled probes (8,9), microplate formats (10–12), reverse dot blot formats (13,14) and automated large scale HLA class 11 typing (15). A common drawback to these methods, however, is the relatively long assay times needed—generally one to two days—and their relatively high complexity and resulting high cost. In addition, the necessity for sample transfers and washing steps increases the chances that small amounts of amplified DNA might be carried over between samples, creating the risk of false positives.

Recently, a molecular typing method using sequence specific primer amplification (PCR-SSP) has been described (16–18). This PCR-SSP method is simple, useful and fast relative to PCR-SSO, since the detection step is much simpler. In PCR-SSP, sequence specific primers amplify only the complementary target allele, allowing genetic variability to be detected with a high degree of resolution. This method allows determination of HLA type simply by whether or not amplification products (collectively called an "amplicon") are present or absent following PCR.

In PCR-SSP, detection of the amplification products is usually done by agarose gel electrophoresis followed by ethidium bromide (EtBr) staining of the gel. Unfortunately, the electrophoresis process takes a long time and is not very suitable for large number of samples, which is a problem since each clinical sample requires testing for many potential alleles. Gel electrophoresis also is not easily adapted for automated HLA-DNA typing.

More recently, HLA-DNA PCR-SSP typing using Ethidium homodimer (EthD) staining without electrophoresis has been described (19–20). These methods still require the transfer of PCR products, and this handling increases the chance that traces of amplified DNA will be transferred from sample to sample, which can lead to contamination and false positives.

In an effort to eliminate the need for sample transfers, a homogeneous method for the detection of PCR amplified products using Ethidium bromide (EtBr) fluorescence detection has been developed (21,22). In this method, ethidium bromide is simply added to the amplification reaction mixture; since the amplification product should be present in a large amount relative to the DNA of the starting sample, ethidium bromide fluorescence in a sample where amplification occurred, i.e. where the target sequence was present, is greater than the fluorescence in a sample where the target sequence was lacking, and amplification did not occur. Unfortunately, the template DNA, partial primer dimer, and primer present in both positive and negative samples represents a substantial background, making the discrimination between positive and negative samples somewhat difficult and unreliable. The end result is that the method has relatively low sensitivity and reproducability. Prior to the present invention, no means for reducing this background effect was known.

ADVANTAGES AND SUMMARY OF THE INVENTION

The present invention comprises new methods for the detection of amplified DNA. More specifically, the present invention comprises the use of post-amplification enzyme digestion of 5'-phosphorylated DNA and single stranded DNA in order to degrade template DNA, partial primer dimer, primer and other DNA. The amplified DNA is not substantially 5'-phosphorylated or single stranded, and therefore substantially escapes degradation. The end result is that when presence of DNA in the remaining sample is then detected, the signal obtained is substantially correlated with the presence of amplified DNA in the sample.

One object of the present invention, then, is to provide a method of detecting amplified DNA in which the background caused by the presence of template DNA, partial primer-dimer, primer and other DNA is substantially reduced.

It is a further object of the invention to provide a method for detection of amplified DNA that has a higher degree of reproducability and sensitivity than those methods available in the prior art.

It is also an object of the invention to provide a method that allows for the detection of amplified DNA in a homogeneous assay, that is, an assay that can be carried out in a single vessel without the need for transfer of any sample components.

As such, it is also an object of the invention to provide a method of detecting amplified DNA in which the risks of sample cross-contamination and resulting false positive results are reduced.

It is an additional object of the invention to provide a method that can allow for reliable, rapid analysis of multiple samples.

It is also an object of the invention to provide a method of detecting amplified DNA that is relatively simple, and likely to result in a relatively low cost per analysis.

It is a further object of the present invention to provide a method for the detection of amplified DNA that is amenable to automation.

In one embodiment of the invention, a method for detecting the presence of one or more target DNA sequences in a sample containing 5'-phosphorylated DNA is provided, which comprises the steps of (a) carrying out enzymatic amplification of one or more portions of the DNA in said sample to produce one or more substantially double-stranded, substantially non-5'-phosphorylated amplification products; (b) adding an enzyme that specifically degrades single stranded DNA and an enzyme that specifically degrades DNA having 5'-phosphorylated ends, and incubating under conditions that permit the activity of said enzymes; and (c) detecting the presence of DNA in the sample.

In more detailed embodiments, the 5'-phosphorylated DNA present in the sample may be biologically-derived, or alternatively may be derived by genetic manipulation in vitro; the steps of the method may be carried out in succession by addition of reagents to the reaction mixture resulting from the previous step, without any intervening purifications or separations; and all steps may be carried out in the same sample vessel, which vessel may be a microtiter plate. Detection of DNA may be quantitative or qualitative, and may involve the use of intercalating fluorophores such as ethidium bromide (EtBr), ethidium homodimer (EthD), Thiazole yellow dimer (YO-YO), Thiazole orange dimer (TO-TO), and thiazole orange monomer (TO-PRO), or by other means. The method may also be carried out by automated devices.

In another embodiment of the invention, a method is provided for detecting the presence of one or more target DNA sequences in a sample containing 5'-phosphorylated DNA, comprising the steps of (a) carrying out primed enzymatic transcription on one or more portions of the DNA in said sample, using one or more primers that do not have 5'-phosphorylated ends; (b) adding to the DNA of said sample an enzyme that specifically degrades single stranded DNA, and incubating under conditions that permit the activity of said enzyme; (c) adding to the DNA remaining after step (b) an enzyme that specifically degrades DNA having 5'-phosphorylated ends, and incubating under conditions that permit the activity of said enzyme; and (d) detecting the presence of DNA in the sample. Because the enzymatic digestion steps are carried out separately in this embodiment, it is possible to use methods other than enzymatic amplification, e.g., primer extension using a non-5'-phosphorylated primer, which extended primer will be substantially converted to a double-stranded, non-5'-phosphorylated DNA upon digestion with the single strand-specific nuclease.

A further embodiment of the present invention provides a method for detecting the presence of one or more target DNA sequences in a sample containing 5'-phosphorylated DNA, comprising the steps of (a) amplifying one or more portions of the DNA in said sample by polymerase chain reaction (PCR) to produce one or more double-stranded, non-phosphorylated amplification products; (b) adding the enzymes lambda exonuclease and Exonuclease I and incubating under conditions that permit the activity of said enzymes; (c) adding an intercalating fluorophore selected from the group of ethidium bromide (EtBr), ethidium homodimer (EthD), Thiazole yellow dimer (YO-YO), Thiazole orange dimer (TO-TO), and thiazole orange monomer (TO-PRO); and (d) detecting the level of fluorescence emitted from the sample when illuminated with an appropriate excitation beam.

More detailed embodiments of the invention comprise the above method wherein said level of fluorescence is compared with the fluorescence levels observed when one or more known samples were analyzed by the same method; and/or wherein PCR amplification is carried out using sequence specific primers, which may be specific for one or more human leukocyte antigens (HLAs).

An additional embodiment of the present invention comprises a homogeneous method for detecting the presence or absence of one or more human leukocyte antigen (HLA) in a sample that is substantially of human biological origin, comprising the steps of (a) using one or more HLA-sequence specific antigens in a polymerase chain reaction (PCR) to amplify one or more portions of the HLA-specific DNA in said sample; (b) adding the enzymes lambda exonuclease and Exonuclease I and incubating under conditions that permit the activity of said enzymes; (c) adding an intercalating fluorophore selected from the group of ethidium bromide (EtBr), ethidium homodimer (EthD), Thiazole yellow dimer (YO-YO), Thiazole orange dimer (TO-TO), and thiazole orange monomer (TO-PRO); and detecting the level of fluorescence emitted from the sample when illuminated with an appropriate excitation beam.

It is additionally an object of the present invention to provide reagents kits that can be used to carry out the methods described.

In one embodiment relating to this object of the invention, a kit is provided for detecting the presence of one or more target DNA sequences in a sample containing 5'-phosphorylated DNA, the kit comprising one or more primers that do not have 5'-phosphorylated ends; an enzyme that specifically degrades single stranded DNA; an enzyme that specifically degrades DNA having 5'-phosphorylated ends; and an intercalating fluorophore selected from the group of ethidium bromide (EtBr), ethidium homodimer (EthD), Thiazole yellow dimer (YO-YO), Thiazole orange dimer (TO-TO), and thiazole orange monomer (TO-PRO).

Further embodiments of the kit of the present invention include kits that further comprise reagent solutions having pH levels and containing one or more reagent selected from the group of ions, cofactors and metabolites such that, upon addition to the reaction vessel, the composition of the resulting solution permits the desired enzymatic reaction to occur; and/or further comprising a thermostable DNA-dependent DNA polymerase, such as Taq polymerase. The primers one such kits may be sequence-specific for one or more portion of one or more human leucocyte antigen (HLA) DNA.

In addition to the foregoing, this invention is more generally useful whenever it is desirable to detect the presence of double-stranded, non-5'-phosphorylated DNA, where single-stranded DNA and 5'-phosphorylated DNA present in that same sample might cause an undesirable background signal.

The appended claims are hereby incorporated by reference as an enumeration of the preferred embodiments.

BRIEF DESCRIPTION OF THE DRAWINGS

FIG. 1 is a schematic illustration of how the enzymatic digestions taught by the present invention provide for a reduction in the presence of background DNAs;

DETAILED DESCRIPTION OF THE INVENTION

Figure 2A:
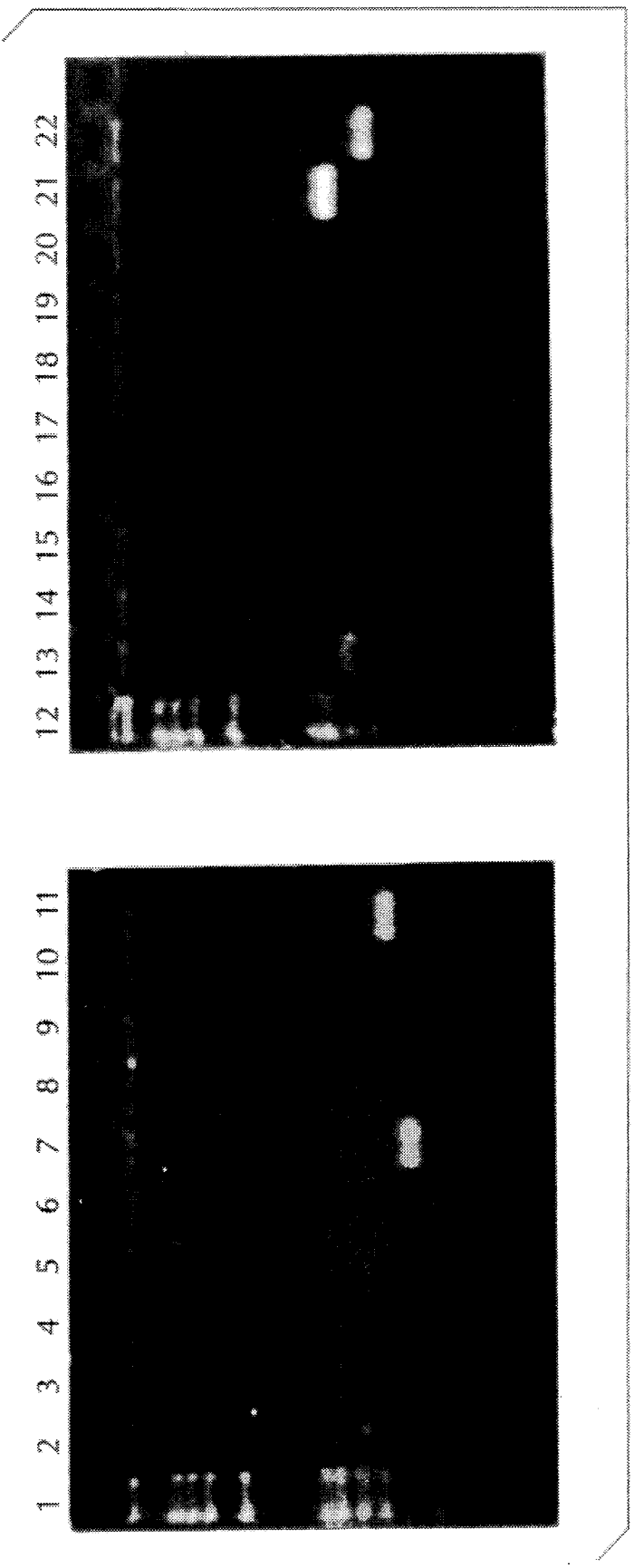
FIGS. 2A–2D are a composite photograph of electrophoretic gels showing that PCR-SSP analysis using HLA-DR sequence-specific primers resulted in specific PCR-product banding patterns, as expected.

The objects and advantages described above, and further objects and advantages that will be apparent to those skilled in the art, stem from a surprising discovery.

In my initial attempts to use PCR-SSP methods described by others that involved the use of fluorescent intercalating dyes, I found that there was an undesirably high signal observed even in samples that did not contain the target sequence. This made it sometimes difficult to distinguish between a positive and a negative result. Although the prior art did not address this problem, I hypothesized that this poor performance was due to high background fluorescence from the template human DNA and unconsumed PCR primers.

Based on this hypothesis, I conceived that it might be possible to use enzyme digestion to eliminate these sources of background fluorescence, and that it might be possible to do so without the need for intermediate purification of the DNA in the sample. Although no single enzyme appeared to be able to achieve this, it was decided that several enzymes with different specificities might be able to act in concert to do so.

The first enzyme selected, Lambda exonuclease, is known to selectively digest the phosphorylated strand of double stranded DNA (27). Because biologically-derived DNA has at least one strand that is substantially 5'-phosphorylated, it was hoped that digestion with this enzyme would remove one strand of the template DNA, while leaving the PCR amplified products substantially unaffected, as they substantially lack the 5'phosphate. However, because of the potentially great length of the human template DNA, it was unclear whether this digestion would have any significant effect.

In a subsequent step, in hope of then digesting any resulting single-stranded template DNA resulting from the first digestion and also removing any unconsumed primer or other single-stranded background DNA, the resulting sample was further digested by Exonuclease 1. Exonuclease I is known to digest single-stranded DNA, but not double-stranded DNA. Although single stranded DNA is not generally expected to fluoresce in the presence of intercalating dyes because those dyes only cause fluorescence of double-stranded DNA, I had hypothesized that small regions of secondary structure might cause a significant background if they were able, singly or in combination, to form small regions of hybridization. It was therefore hoped that this digestion would provide a further diminution of the background.

As the examples appended hereto illustrate, the combined use of these two enzymes gave a surprising degree of reduction in background fluorescence, thus substantially increasing the difference between the fluorescence of positive and negative samples. Subsequent studies also demonstrated that it was possible to combine these digestions into a single step, thus providing for the first highly sensitive, highly reproducible homogeneous method for detecting amplified DNA.

The overall scheme of the present invention is illustrated in FIG. 1. The left side of FIG. 1 illustrates that following PCR amplification, positive samples (i.e., those containing the target sequence) contain amplified DNA, and also contain the original sample template DNA and unutilized primers. Negative samples, (i.e., those not containing the target sequence) do not contain amplified DNA, but do contain the template DNA and the added primers. In prior art methods, fluorescent dye was added at this point, and fluorescence was measured. Because of the presence of template and primer DNA in both positive and negative samples, substantial fluorescence occurred in both, and discerning the increase in fluorescence in positive samples relative to negative samples was problematic.

Referring again to FIG. 1, note that after the step labeled "Selective Enzyme Digestion", the situation has considerably changed. Now, the positive samples contain primarily the amplified DNA, the template and primer having been substantially degraded. Exonuclease I digestion may also have helped to digest partial primer dimers that had single stranded regions. In negative samples, there is no amplified DNA, and the template and the primers have similarly been substantially degraded. When a fluorescent dye is then added, the positive sample, containing double-stranded amplified DNA, fluoresces strongly; whereas the negative sample, lacking substantial quantities of DNA, fluoresces weakly or not at all. When this result is compared to the results obtained using prior art methods, the advantages of this reduction in the background signal will be readily appreciated by those skilled in the art.

The foregoing scheme is based upon the facts that PCR amplicons have 5'-OH termini, since their 5' ends contain synthesized primer; and that in contrast, human template DNA has 5'-phosphorylated ends. Since Lambda exonuclease can digest only phosphorylated DNA, it selectively digests the double stranded human DNA, presumably down to single stranded DNA. Both the single stranded human DNA and PCR primers are then degraded by Exonuclease 1. In contrast, PCR amplified products, which are double stranded and have 5'-OH ends, are not affected by these enzymes.

It is important to an understanding of the present invention to note that all technical and scientific terms used herein, unless otherwise defined, are intended to have the same meaning as commonly understood by one of ordinary skill in the art; that techniques employed herein are also those that are known to one of ordinary skill in the art, unless stated otherwise; and that publications mentioned herein are incorporated by reference.

It is also important to note that reference to particular buffers, reagents and the like, or to some subclass of same, is not intended to be limiting, but should be read to include all such related materials that one of ordinary skill in the art would recognize as being of interest or value in the particular context in which that discussion is presented. For example, it is often possible to substitute one buffer system for another, etc., such that a different but known way is used to achieve the same goals as those to which the use of a suggested method, material or composition is directed.

It is additionally important to recognize that although Lambda exonuclease and Exonuclease 1 are used in the examples provided herein, the present invention is not limited to the use of those particular enzymes. Any enzymes that have comparable activity may be substituted, and such substitutions are within the scope of the present invention. One source of such different enzymes may be to derive enzymes that degrade 5'-phosphorylated DNA or single-stranded DNA from different organisms than are the enzymes used in the examples. Alternatively, enzymes structurally and kinetically distinct from those mentioned may exist that have similar activity. For example, the enzyme S1 nuclease also is known to digest single-stranded DNA, and could be substituted for Exonuclease 1.

Furthermore, even though human HLA antigen-specific primers are used in the examples herein, the present invention is widely applicable to testing for the presence of an enormous spectrum of specific gene sequences. Moreover, it is not necessary that PCR-SSP be the method used; the present invention is of utility anytime amplification is carried out, and it is desirable to determine whether the reaction has occurred or not, or to what degree it has occurred. In addition, it is important to note that although PCR is the amplification method used in the examples and preferred embodiments described herein, the present invention is not dependant thereon, and the use of the enzyme digestions described herein in conjunction with other amplification methods, both those known and not yet known, is well within the scope of the present invention.

Finally, it is important to note that the present invention is not limited to the use of all of the above-described discoveries or embodiments together. Although combining them may indeed be preferred, it is not necessary to the invention that all aspects be used simultaneously.

It is necessary to a clear understanding of the present invention to understand that a number of the terms used herein are not intended to be limiting, even though common usage might suggest otherwise. For example, where the term "transcription" is used, this should be viewed broadly, e.g., to include the copying of one strand of DNA to form a second strand, and also to include iterative methods such as DNA amplification. The term "portions" should similarly be viewed broadly, and would include the case where a "portion" of a DNA strand is in fact the entire strand.

Where used herein, the term "sensitivity" is meant to refer to the ability of an analytical method to detect small amounts of analyte. Thus, as used here, a more sensitive method for the detection of amplified DNA, for example, would be better able to detect small amounts of such DNA than would a less sensitive method.

The term reproducibility as used herein refers to the general ability of an analytical procedure to give the same result when carried out repeatedly on aliquots of the same sample.

The term "target sequences" refers to sequences in a sample template DNA, portions of which may be of particular interest. Detection of the presence or absence of target sequences is, for example, generally the object of the PCR-SSP method.

The term "amplicon" is used herein to mean a population of DNA molecules that has been produced by amplification, e.g., by PCR.

In describing the present invention, frequent mention is made to detecting the presence of DNA in the enzyme-treated sample. It is important to note that such detection can be carried out in a variety of ways, all of which are within the scope of the present invention. Such methods may detect specific sequences, detect specific secondary structures, detect some other subset of the DNA population, or simply detect total DNA. For example, the DNA remaining after enzyme digestion can be detected by a dye that intercalates between base pairs in double-stranded DNA, as described in the examples that follow. Alternatively, it is also possible, for example, to detect the presence of DNA by measuring the absorbance of ultraviolet light by the sample, or by detecting the binding of sequence-specific, fluorescently or radioactively labeled DNA probes. These are offered as but a few examples, and alternate means by which DNA can be detected will be readily apparent to those skilled in the art.

In addition, it is also important to note that detection of the presence of DNA may be qualitative or quantitative. The examples describe homogeneous assays in which detection of DNA was qualitative, i.e., where the samples were tested for the presence or absence of amplified DNA products. However, many methods of quantitative DNA analysis are known in the art, and such methods can be used in the present invention to considerable advantage. For example, by detecting the absolute or relative quantity of amplified DNA in a sample, it should be possible to determine the absolute or relative number of copies of a target sequence that were in the original template DNA sample. This could be important, for example, when it is desirable to determine whether one or both of the alleles in the chromosomes of an individual carry a defect associated with a genetic disease. Such an analysis could be used to determine, for example, whether an as-yet unborn child will have the phenotype associated with a recessive genetic defect, or to determine what pattern of familial gene transmission can be anticipated among an individual's offspring. These quantitative approaches and their uses are well within the scope of the present invention.

The use of the present invention is not limited to the treatment and detection of amplified DNA, but extends to any situation wherein it is desired to detect the presence of non-5'-phosphorylated DNA in the presence of 5'-phosphorylated DNA and single-stranded DNA. Many such situations can be envisioned. For example, it is possible to add a non-5'-phosphorylated DNA probe to a sample of heat-melted 5'-phosphorylated DNA, which will result in the creation of double-stranded sequences that are flanked on one or both ends by single-stranded sequences; preferably, the 5'-phosphorylated end of the template will extend beyond the probe and therefore be single-stranded. The sample could then be digested with an enzyme that specifically degrades single-stranded DNA, which would trim off the single stranded ends and degrade any remaining primer. Next, the sample could be treated with an enzyme that degrades 5'-phosphorylated DNA; this would degrade any re-annealed template DNA, and if this latter digestion is carried out in a manner that permits the continued activity of the single stranded nuclease, this should degrade any single-stranded sequences that result from the 5'-phosphorylated DNA degrading enzyme. Detection of the DNA remaining after this digestion will be indicative of the presence or absence of the target sequence in the template DNA. This example is offered only to illustrate that not only can amplified DNA be detected by the present methods, but DNA strands created by probe hybridization and other methods can also be advantageously detected by the present invention. Many other embodiments that do not involve DNA amplification can also be envisioned by those skilled in the art, and are within the scope of the present invention.

In carrying out the methods of the present invention, it is not necessary that the two enzyme digestions be done simultaneously, although this may be the most convenient approach in many cases, but they can also be done separately. The digestions also need not be done in any particular order if done separately, although using one or the other first may have certain additional advantages, as in the example of the paragraph above. In addition, it is not necessary to halt the activity of one enzyme before adding the other, as continued activity of the first added enzyme may not, in a given experiment, be detrimental, and may actually be beneficial. On the other hand, if desired, the activity of the first enzyme can be halted before adding the second, for example, by heating the sample to a temperature that denatures the first enzyme and then cooling before adding the second enzyme. Many other ways of inactivating the first enzyme can also be envisioned by those skilled in the art. Of course, the second enzyme could also be inactivated if desired, e.g., in a situation where a DNA probe will subsequently be added.

The practice of the present invention does not require that digestion by the enzymes described be carried to completion. Although fairly complete digestion may in many instances be preferred, one developing a specific application of the present invention may find that more limited digestion provides a sufficient reduction of the background, and that the increased assay time or increased cost of a more complete digestion are not justified by the incremental improvement in the assay that is achieved.

Although the function of the present invention has here been attributed to the digestion of a template 5'-phosphorylated DNA by one enzyme and single-stranded probe and other single-stranded DNA by another, it is important to note that the invention is not limited in its application to situations where primers or probes are added. It is possible that in some situations, it will desirable to detect the presence of non-5'-phosphorylated DNA in a sample containing 5'-phosphorylated DNA and no probe. In such an instance, the single-stranded nuclease still is expected to be important to use along with the 5'-phosphorylated DNA; as the 5'-phosphorylated DNA-degrading enzymes "chews" in from the ends of one strand of a double strand, it likely leaves behind single-stranded portions that can be degraded by the second enzyme.

The 5'-phosphorylated DNA expected to serve as a template in various embodiments of the present invention may be DNA of biological origin, which is naturally 5'-phosphorylated. However, it is also possible that 5'-phosphorylated DNA may be created by a variety of synthetic means. For example, one might use 5'-phosphorylated probes to amplify a large region of a non-5'-phosphorylated template DNA, and then use non-5'-phosphorylated primers to amplify portions thereof. It is also possible to enzymatically phosphorylate a given DNA sample. A variety of other means by which the 5'-phosphorylated DNA in a given sample might be originated can also be envisioned.

The detection of DNA after enzyme digestion is accomplished in the following examples by the addition of an intercalating dye. In the examples, the dye was added to the samples after enzyme digestion. However, this is not meant to be limiting, as it is possible to add the dye at any step, as will be readily apparent to those skilled in the art.

In describing the present invention, some embodiments are described as being "homogeneous" methods. This term refers to the potential that the entire reaction can be carried out without the need for intermediate purification or transfer of the sample or components thereof.

In the examples, total DNA was first purified from biological samples, and this was then used as an amplification template. This should not be viewed as a limitation, as it may not be necessary in a given circumstance to purify the DNA away from other biological materials or other components in a starting sample.

Although definitions of some or all of the following abbreviations may be set forth elsewhere herein, and although most if not all are well recognized by those skilled in the art, their meaning are set out hereinbelow for convenient reference.

PCR: Polymerase Chain Reaction
HLA: Human Leukocyte Antigen
SSP: Sequence Specific Primer
SSO: Sequence specific Oligonucleotide probe
RFLP: Restriction Fragment Length Polymorphism
EtBr: Ethidium Bromide
EthD: Ethidium homodimer
YO-YO: Thiazole yellow dimer
TO-TO: Thiazole orange dimer
TO-PRO: Thiazole orange monomer The examples below describe in detail the use of a homogeneous fluorescent detection method for HLA-SSP typing. Through this combination of enzyme treatments, background fluorescence in PCR reactions was decreased to about one third of that detected untreated controls. The use of a new class of highly fluorescent dimeric asymmetric cyanine fluorescence dyes that have a higher affinity for double stranded DNA than EtBr and EthD (23,24) augmented this result. Furthermore, this detection method is homogeneous and does not require the transfer of PCR products between microplates. PCR amplification, enzyme digestion, and detection was carried out in the same well of the same plate without transfer, and fluorescence was measured from that same well using a microplate fluorescence reader, all within about 30 minutes. Elimination of sample transfer through the utilization of microplate format PCR amplification and detection made possible the faster, easier and more accurate method for detection of PCR amplified sample. This approach is highly compatible with automation and computerized data analysis. This progression towards ease of use, high performance, and automation should make homogeneous fluorescence detection methods especially suitable for HLA typing laboratories and reference laboratories that deal with large numbers of samples.

This method will be useful for the detection of PCR amplified products not only for HLA typing, but also for infectious disease testing of viral and bacterial DNA (e.g., HIV, HTLV, Herpes) and for detection of mutations. Since blood borne virus detection requires detection of a few target copies per ~$10^5$ human cells (28), detection must be sensitive and specific. In earlier homogeneous PCR detection methods, background fluorescence made it difficult to detect a few copies of target DNA in large number of cells (21). By using the improvements described herein, background fluorescence can be greatly reduced and may be lowered sufficiently to allow detection and quantification of even very low abundance targets.

The described embodiments, examples and instructions are not intended in any way to be limiting, as it should be readily apparent to those skilled in the art how alternative means might be used to achieve the results that this invention provides.

The following experimental methods, having been used by us to demonstrate and illustrate the present invention, are described in substantial detail hereinbelow. However, these details are not intended to be limiting, and those skilled in the art will appreciate that many other embodiments of the present invention are possible.

Materials and Methods

DNA Extraction

DNA samples were extracted from peripheral blood leukocytes and homozygous typing cell lines from the Tenth workshop panel (25). Cells were lysed and digested by RNase and Protease K treatment and their DNA extracts were purified by salting out and ethanol precipitation (the protocol used was derived from a genomic DNA isolation Kit obtained from the company Bio 101). Each aliquot of extracted DNA was dissolved in $H_2O$ at a concentration of 15 µg/ml.

Preparation of sequence-Specific primers

The primers used were designed to obtain highly specific and sensitive allele- and group-specific amplification for DR1–DR1 8 as well as DR52 and DR53. Sequence specific primer pairs used for DRB1, DRB3 and DRB4 typing are shown in Table 1. Primers were

TABLE 1

Primer pairs for PCR-SSP HLA-DR typing

| Primer Pair name | Sequence I.D. No. | Sequence | Amplified HLA-DR Alleles | HLA-DR Serological Specificities |
|---|---|---|---|---|
| DRBAMP-1 | 1 | 5'TTC TTG TGG CAG CTT AAG TTT3' | DRB1*0101.0103 | DR1 |
|  | 2 | 5'CCG CTG CAC TGT GAA GCT CT3' |  |  |
| DRBAMP-2 | 3 | 5'CCT GTG GCA GCC TAA GAG G3' | DRB1*1501–1503 | DR15(2) |
|  | 4 | 5'CCG CTG CAC TGT GAA GCT CT3' | 1601–1602 | DR16(2) |
| DRBAMP-15 | 5 | 5'CCT GTG GCA GCC TAA GAG G3' | DRB1*1501–1503 | DR15(2) |
|  | 6 | 5'TCC ACC GCG GCC CGC GC3' |  |  |
| DRBAMP-16 | 7 | 5'CCT GTG GCA GCC TAA GAG G3' | DRB1*1601–1602 | DR16(2) |
|  | 8 | 5'ACC GCG GCG CGC CGC CTG TCT3' |  |  |
| DRBAMP-3 | 9 | 5'CAC GTT TCT TGG AGT ACT CTA C3' | DRB1*0301–0303 | DR17(3) |
|  | 10 | 3'GCA GTA GTT GTC CAC CCG GC3' |  | DR18(3) |
| DRBAMP-17 | 11 | 5'CAC GTT TCT TGG AGT ACT CTA C3' | DRB1*0301,1101–1104[a] | DR17(3).DR11 |
|  | 12 | 5'AGC TCC GTC ACC GCC CGG A3' | 1201–1202[a] | DR12 |
|  |  |  | 1301–1306(except 1303)[a] | DR13 |
| DRBAMP-18 | 13 | 5'CAC GTT TCT TGG AGT ACT CTA C3' | DRB1*0302–0303 | DR18(3) |
|  | 14 | 5'CTC CTG GTT ATG GAA GTA TCT C3' |  |  |
| DRBAMP-4 | 15 | 5'GTT TCT TGG AGC AGG TTA AA3' | DRB1*0401–0412 | DR4 |
|  | 16 | 5'CCG CTG CAC TGT GAA GCT CT3' |  |  |
| DRBAMP-11 | 17 | 5'CAC GTT TCT TGG AGT ACT CTA C3' | DRB1*1101–1104 | DR11 |
|  | 18 | 5'CTG GCT GTT CCA GTA CTC CT3' |  |  |
| DRBAMP-12 | 19 | 5'CAC GTT TCT TGG AGT ACT CTA C3' | DRB1*1201–1202 | DR12 |
|  | 20 | 5'GCT GTT CCA GGA CTC GGC GA3' |  |  |
| DRBAMP-7 | 21 | 5'CCT GTG GCA GGG TAA GTA TA3' | DRB1*0701–0702 | DR7 |
|  | 22 | 5'CCC GTA GTT GTG TCT GCA CAC3' |  |  |
| DRBAMP-8 | 23 | 5'GTA CTC TAC GGG TGA GTG TT3' | DRB1*0801–0805 | DR8 |
|  | 24 | 5'CTG CAG TAG GTG TCC ACC AG3' |  |  |
| DRBAMP-9 | 25 | 5'CGG AGC GGG TGC GGT AT3' | DRB1*0901 | DR9 |
|  | 26 | 5'CCC GTA GTT GTG TCT GCA CAC3' |  |  |
| DRBAMP-10 | 27 | 5'CGG TTG CTG GAA AGA CGC G3' | DRB1*1001 | DR10 |
|  | 28 | 5'CCG CTG CAC TGT GAA GCT CT3' |  |  |
| DRBAMP-13A | 29 | 5'CAC GTT TCT TGG AGT ACT CTA C3' | DRB1*1301,1302,1304 | DR13 |
|  | 30 | 5'GTC CAC CGC GGC CCG CTC3' | 1102–1103[a] | DR11 |

TABLE 1-continued

Primer pairs for PCR-SSP HLA-DR typing

| Primer Pair name | Sequence I.D. No. | Sequence | Amplified HLA-DR Alleles | HLA-DR Serological Specificities |
|---|---|---|---|---|
| DRBAMP-13B | 31 | 5'CAC GTT TCT TGG AGT ACT CTA C3' | DRB1*1303,1304 | DR13 |
|  | 32 | 5'CTG TTC CAG TAC TCG GCG CT3' | 0801[a],0803[a],0805[a] | DR8 |
| DRBAMP-14A | 33 | 5'CAC GTT TCT TGG AGT ACT CTA C3' | DRB1*1401,1404,1405,1407 | DR14 |
|  | 34 | 5'CCA CCT CGG CCC GCC TCC3' | 1408 |  |
| DRBAMP-14B | 35 | 5'CAC GTT TCT TGG AGT ACT CTA C3' | DRB1*1402,1406,1409 | DR14 |
|  | 36 | 5'CAC CGC GGC CCG CCT CTG3' |  |  |
| DRBAMP-52 | 37 | 5'CCC CAG CAC GTT TCT TGG AGC T3' | DRB1*0101,0201-0202,0301 | DR52 |
|  | 38 | 5'CCG CTG CAC TGT GAA GCT CT3' |  |  |
| DRBAMP-53 | 39 | 5'AGC GAG TGT GGA ACC TGA T3' | DRB4*0101 | DR53 |
|  | 40 | 5'CTC CAC AAC CCC GTA GTT GTA3' |  |  |

[a]Cross amplification synthesized on a DNA synthesizer (Model 380 B, Applied Biosystem) and purified by Oligonucleotide Purification Cartridges (Applied Biosystems).

DNA Amplification

The PCR reaction mixture (25 µl) consisted of 200 ng purified sample DNA, PCR buffer (50 mM KCI, 2 mM MgCI2, 10 mM Tris-HCI, 0.1% Triton X-100, pH 9.0), 200 µM each dATP, dCTP, dGTP and dTTP, 0.5 µM each sequence specific primer pair (0.2 µM DRAMP-14A primer pair), and 0.5 units Sequence grade Taq DNA polymerase (Promega). Reagent, enzyme and sample DNA were placed in 96 well polycarbonate microplates with plate covers (MJ Research) and covered with 7 µl of mineral oil to limit evaporative losses and prevent contamination. PCR amplifications were carried out in a PTC-100-96 V thermal cycler (MJ research). The temperature program was: first denaturation step at 94° C. for 2 min., followed by 30 cycles of denaturation at 94° C. for 30 s, then annealing at 61° C. for 50 s and extending at 72° C. for 30 s.

Electrophoresis

To confirm PCR amplification, PCR products were checked on 3% Nusive agarose gels (FMC BioProducts) electrophoresed in 1×TBE buffer. 10 µl of each PCR reaction was mixed with 5 µl of dye glycerol mix (30% glycerol, 0.25% Bromphenol blue) and loaded on the gels. Double-stranded DNA bands were visualized using EtBr (0.5 g/ml).

Enzyme Treatment

After PCR amplification, 5 units of Lambda exonuclease (Pharmacia) in 2 µl PCR buffer and 10 units of Exonuclease I (United States Biomedical) in 2 µl PCR buffer were added to 15 µl of each PCR reaction mixture in the microplate well. The mixtures were incubated at 37° C. for 25 min and denatured at 70° C. for 5 min. in the thermal cycler.

Fluorescence detection

Fluorescent dyes Ethidium bromide, Ethidium homodimer, TO-PRO, TO-TO and YO-YO were purchased from Molecular Probe. Each was diluted and 1 µl was added to each microwell after enzyme treatment to yield final dye concentrations as described herein. Fluorescence was detected using a Microplate fluorescence reader (FLUO-ROSCAN 11, ICN Biomedicals). The polycarbonate microplate wells were nested within the DYNATECH Micro FLUOR plate (U-bottom, edge trimmed) to enhance signals and to prevent fluorescent signal leaking between wells.

HLA DNA typing and serological typing of clinical samples

PCR amplification of PCR samples was done in polycarbonate microplates (25 µl reaction mix) with 20 sequence-specific primers for HLA-DR typing. Ten microliters of PCR products were analyzed by electrophoresis to confirm the amplification and 15 µl of PCR products were detected by homogeneous fluorescence detection following enzyme treatment. One microliter of 100 µM YO-YO was added to each well and the fluorescence was measured at 538 nm following excitation at 485 nm. Serological typings for the HLA-DR locus were carried out by standard microlymphocytotoxicity methods (26).

EXAMPLE 1

PCR-SSP amplification specificity

Figure 2B:
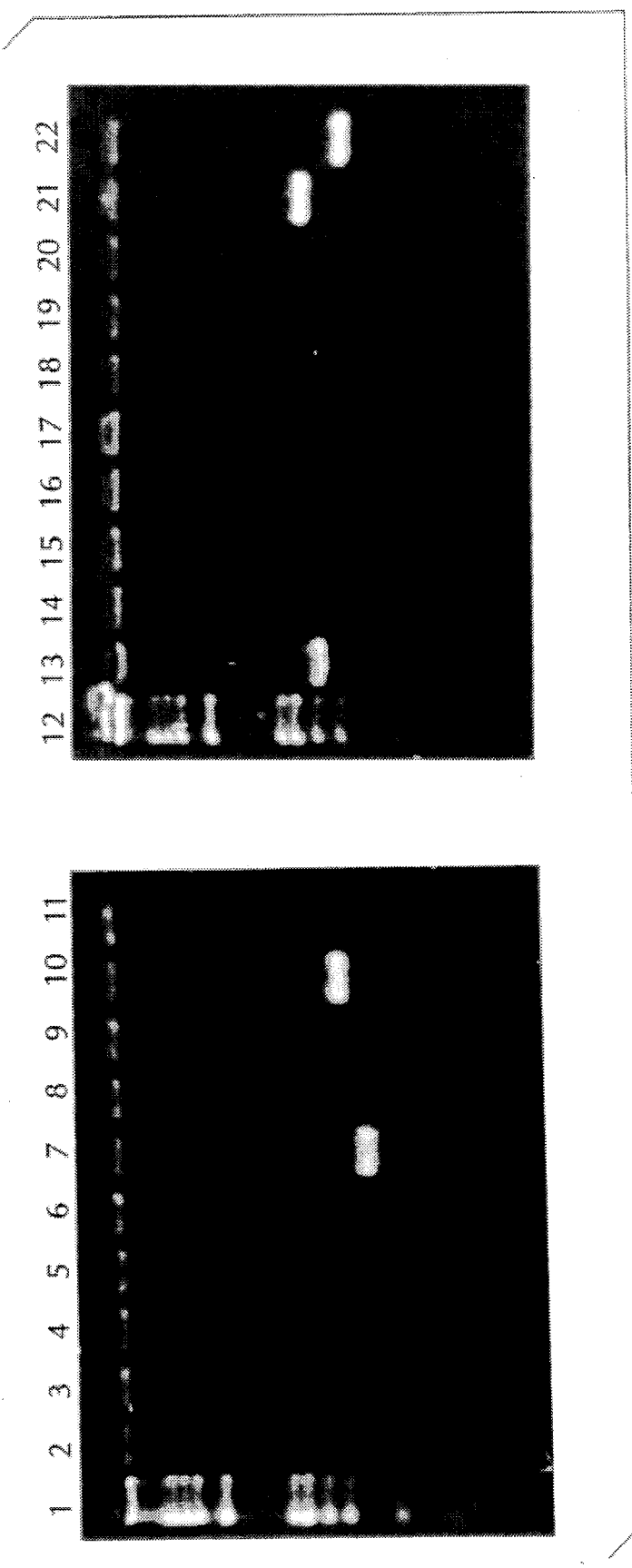
Figure 2C:
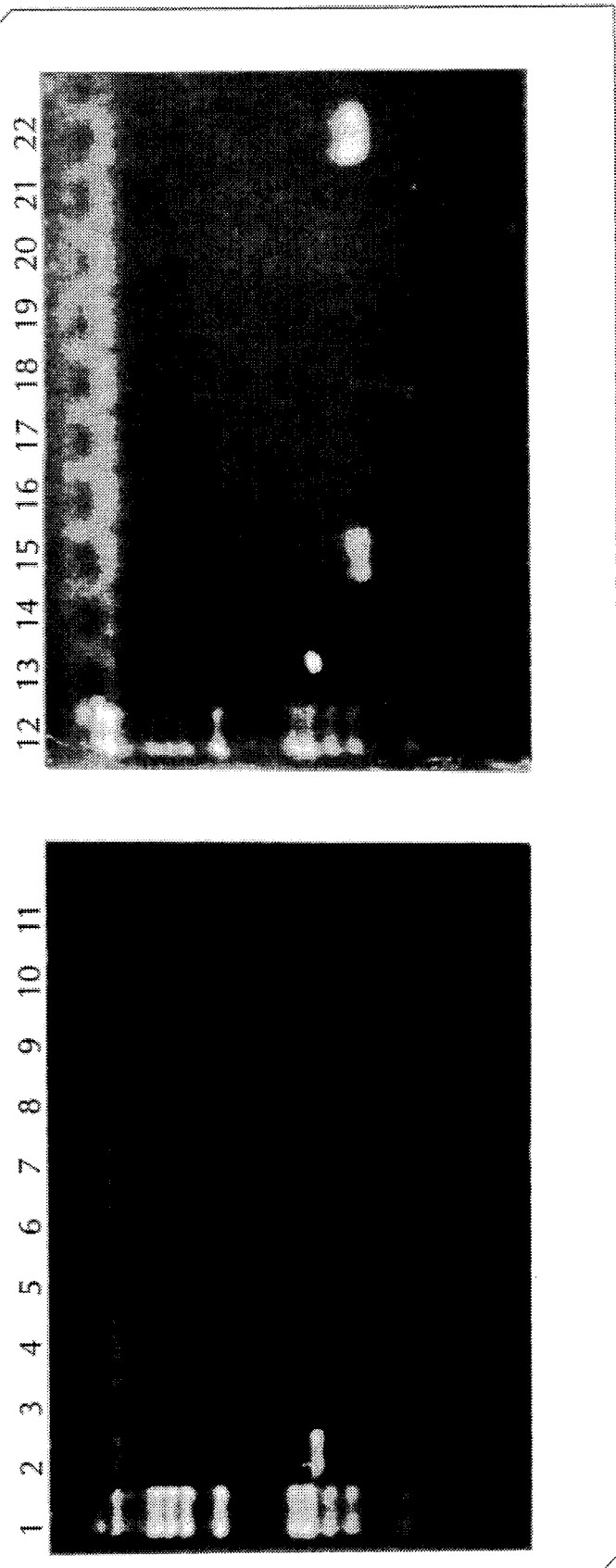
Figure 2D:
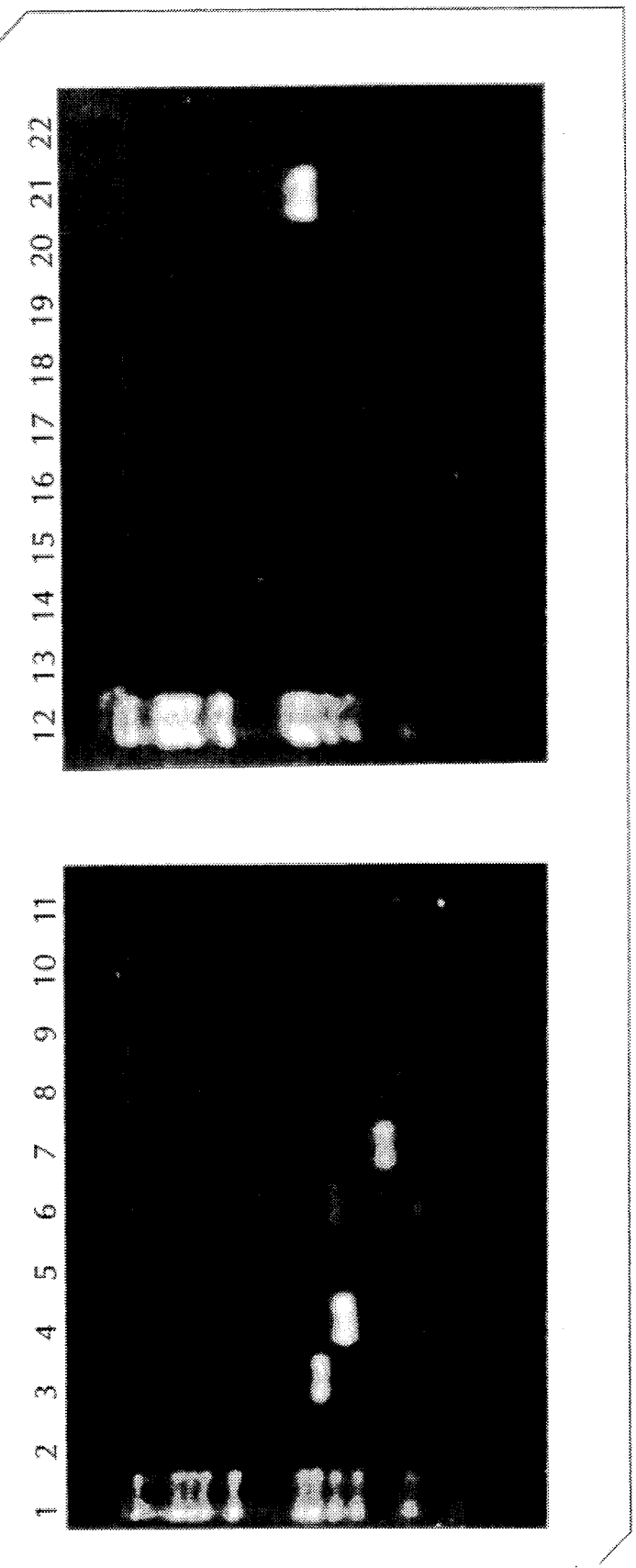

DNA samples from four clinical samples were subjected to 30 cycles of PCR with the twenty sequence-specific primers of Table 1, which were designed to detect the DRB1 alleles *0101-0103, 1501-3, 1601-2, 0301-0303, 0401-0412, 1101-1104, 1201-1202, 1301-1304, 1401-1402, 1404-1409, 0701-0702, 0801-0805, 0901, 1001, DRB3*0101, 0201-0202, 0301, and DRB4*0101. The HLA types of the four clinical samples were: (A) DR7, DR12, (B) DR7, DR11, (C) DR1, DR9, and (D) DR15, DR17. Each clinical specimen was tested with all 20 PCR primers, and 10 µl aliquots of each were run on agarose gels, as shown in FIG. 2. The lanes of the gels in FIG. 2 are as follows: OX 174 HaeIII-digested DNA molecular weight marker (lanes 1 and 12), DRBAMP -1 (lane 2), DRBAMP -2 (lane 3), DRBAMP-15 (lane 4), DRBAMP-16 (lane 5), DRBAMP-3 (lane 6), DRBAMP-17 (lane 7), DRBAMP-18 (lane 8), DRBAMP-4 (lane 9), DRBAMP-11 (lane 10), DRBAMP-12 (lane 11), DRBAMP-7 (lane 13), DRBAMP-8 (lane 14), DRBAMP-9 (lane 15). DRBAMP-10 (lane 16), DRBAMP-13A (lane 17), DRBAMP-13B (lane 18), DRBAMP-14A (lane 19), DRBAMP-14B (lane 20), DRBAMP-52 (lane 21), and DRBAMP-53 (lane 22). These results clearly show that specific amplification products were obtained in using each primer.

Reduction of background fluorescence

Multiple aliquots of DNA extract from a DR 9-specific human blood sample were amplified as described above using DRBAMP-1, DRBAMP-4, DRBAMP-9, and DRBAMP-12 primers, and 15 µl of each the resulting reaction mixtures were (a) left untreated, (b) digested with Lambda exonuclease, (c) digested with Exonuclease I, or (d) treated with Lambda exonuclease and Exonuclease. Digestions were carried out directly in the microtiter plate, and 1 µl of TO-PRO was added to each well. Fluorescence was then measured at 538 nm following excitation at 485 nm.

The results are shown in Table 2. Through the combination of enzyme treatments, background fluorescence in the PCR reactions, apparently due to human DNA and primer, was decreased to about one third of that observed in the untreated control samples. It appears that tended to lose fluorescence at high dye/DNA ratios. At high concentrations, YO-YO was in a suitable dye ratio for

TABLE 2

The effect of enzyme treatment on background fluorescence

| | Human DNA 100 ng/15 µl | Primer 0.4 µM, 15 µl | PCR amplicon HPLC purified 15 µl | DR 9 amplification[a] | | | |
|---|---|---|---|---|---|---|---|
| | | | | DRBAMP-1 | 4 | 9 | 12 |
| No enzyme tratment | 162.1[b] | 80.6 | 670.1 | 161.5 | 170.6 | 644.5 | 166.1 |
| Exonuclease I (10 U) digestion | 144.7 | 2.8 | 667.8 | 87.0 | 83.5 | 635.4 | 83.1 |
| Lambda exonuclease digestion (5 U) | 68.5 | 75.6 | 608.3 | 149.2 | 160.1 | 554.5 | 161.3 |
| Exonuclease I (10 U) + Lambda exonuclease digestion (5 U) | 43.8 | 2.2 | 615.0 | 71.5 | 63.9 | 557.1 | 60.2 |

[a]PCR products from a complete PCR-SSP amplification. (PCR-SSP of DR9 panel cell DNA with DRBAMP-1, DRBAMP-4, DRBAMP-9 and DRBAMP-12 primers)
[b]After enzyme treatment, 1 µl of 100 µM TO-PRO was added to each sample. Fluorescence was measured at 538 nm following excitation at 485 nm.

Exonuclease 1 digestion had the most dramatic effect, but Lambda Exonuclease digestion also had a measurable effect; the combination of the two was clearly preferable.

EXAMPLE 2

Analysis using different fluorescent dyes

Figure 3A:
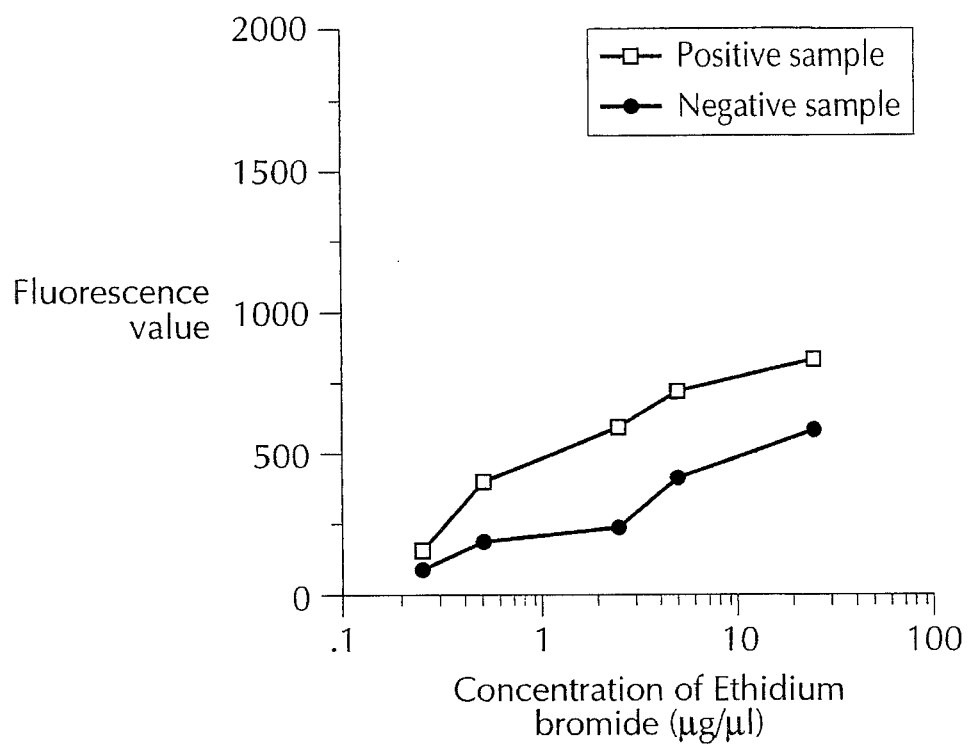
FIGS. 3A–3E show the results of a comparison of the fluorescence obtained when PCR-SSP HLA typing was carried out using the homogeneous method of the present invention and several different fluorescent dyes at various concentrations, and comparing the results obtained using positive and negative samples.
Figure 3B:
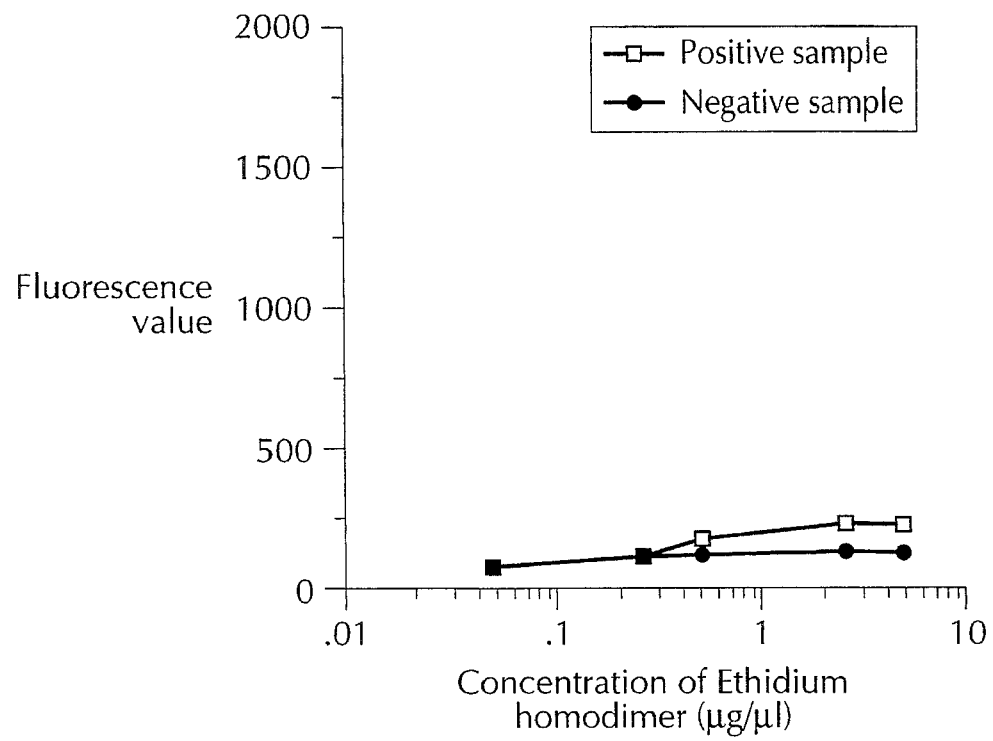
Figure 3C:
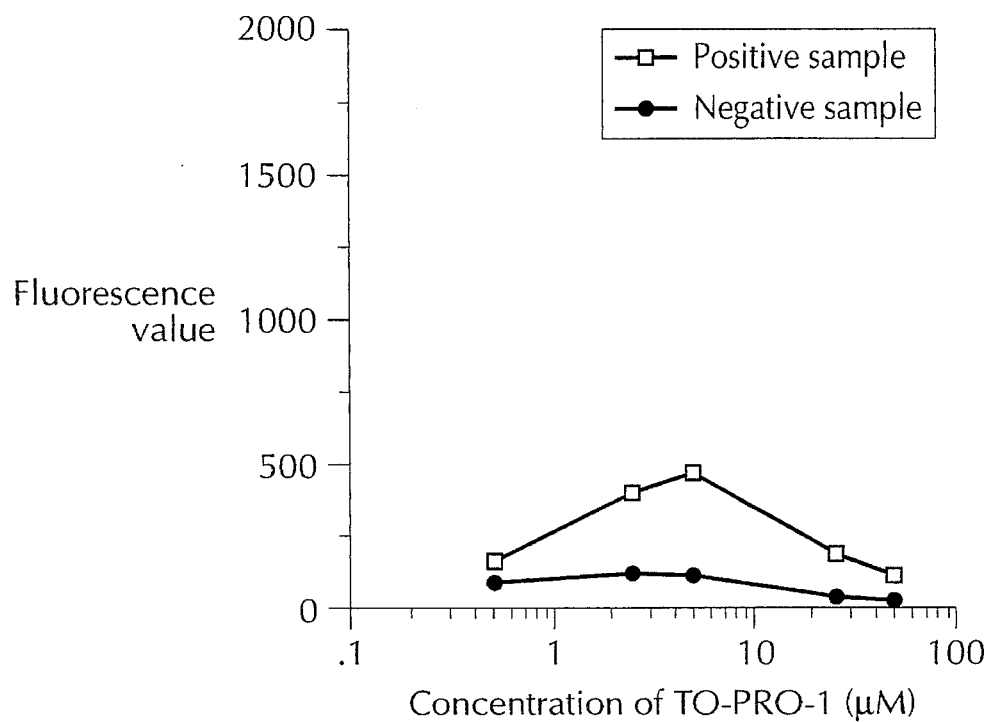
Figure 3D:
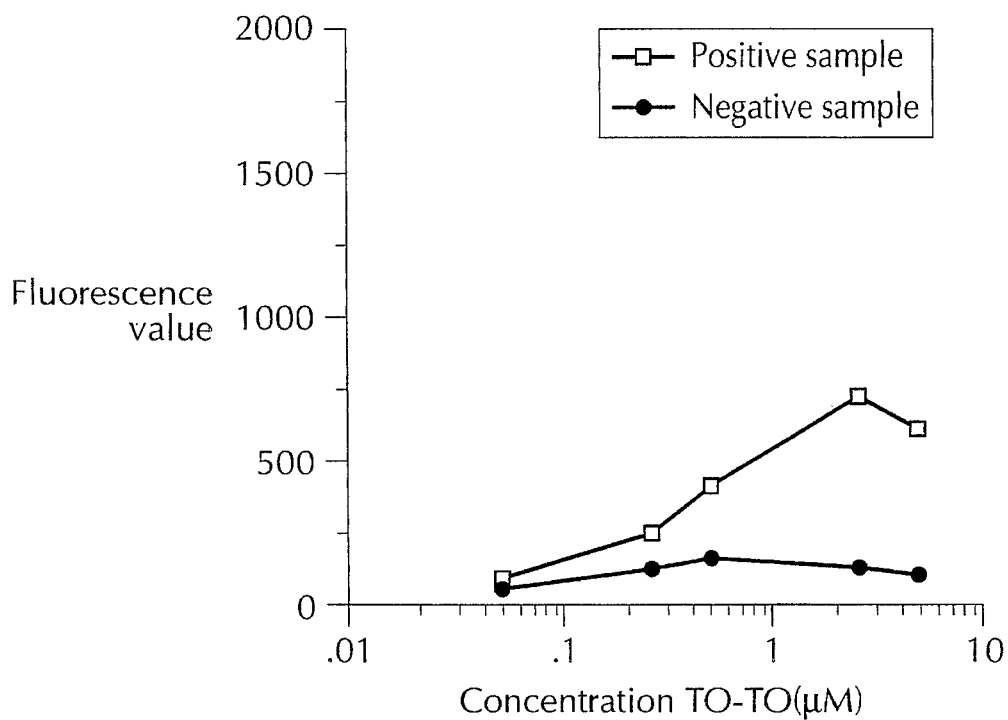
Figure 3E:
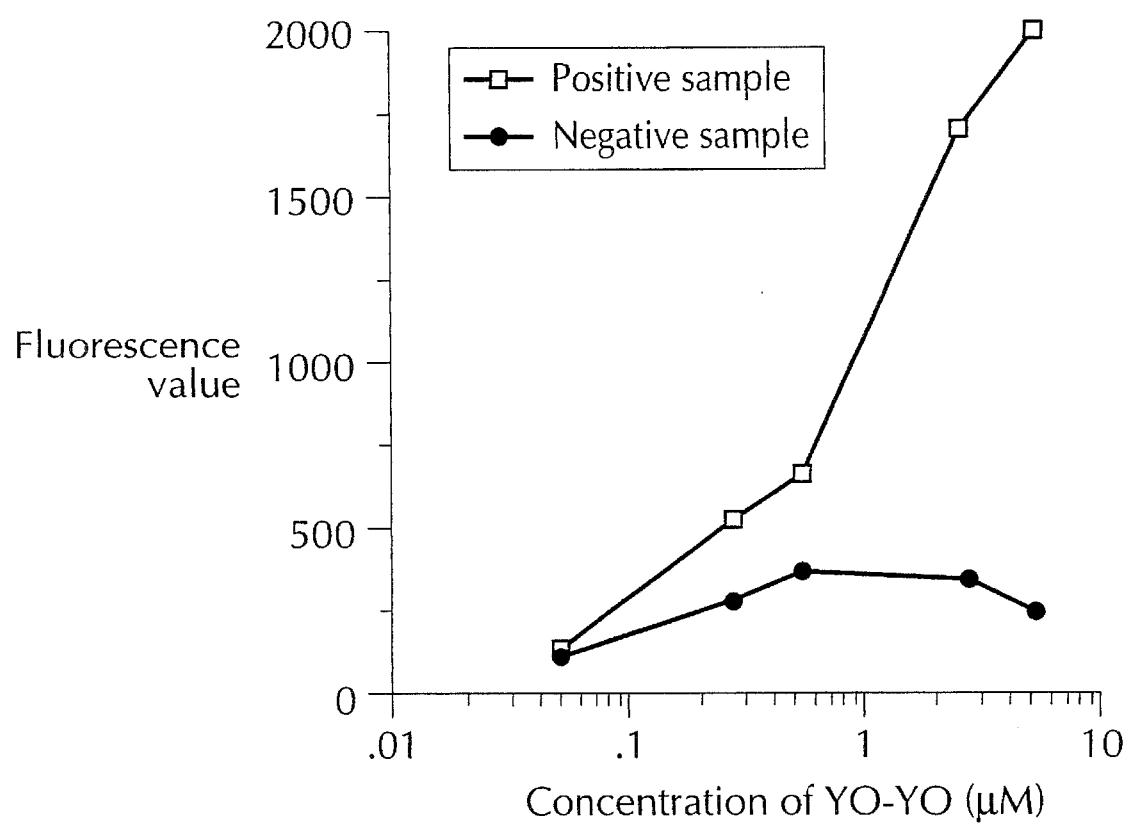

Several fluorescent dyes for nucleic acid staining were compared for applicability to homogeneous detection of PCR-SSP samples after enzyme treatment; the results are shown in FIG. 3. Fluorescent dyes ethidium bromide (A), ethidium homodimer (B), TO-PRO (C), TO-TO (D), and YO-YO (E) were tested over a range of dye concentrations, and each dye was tested using positive and negative PCR-SSP samples. The positive samples contained DNA from a DR9 sample (cell line DKB) amplified with DRBAMP-9 primers; the negative samples contained the same DNA but were amplified with DRBAMP-1 primers which were not complementary. For each dye concentration tested, 15 µl of the amplified reactions were treated with 5 units of Lambda exonuclease and 10 units of Exonuclease 1. After enzyme treatment, 1 µl of dye was added to each well and the fluorescence was measured. For EtBr and EthD, excitation was at 544 nm and emission was at 590 nm; for TO-PRO, TO-TO and YO-YO, excitation was at 485 nm and emission was at 538 nm.

Although EtBr is the most common fluorescent dye used to visualize DNA following gel electrophoresis, EtBr appeared to fluoresce even in the absence of double stranded DNA, and the fluorescence ratios between positive and negative samples were not easily distinguished. EtHD had lower background fluorescence than EtBr, but sensitivity for DNA detection was relatively poor.

Three relatively new highly fluorescent dyes, TO-PRO, TO-TO, and YO-YO (23,24) were also compared. The best performance was seen with YO-YO. Interestingly, this dye positive sample; for negative samples, the fluorescence tended to decrease. This apparent quenching actually contributed to an improvement in the signal difference between positive and negative samples.

These results show that some of the recently developed dyes were more sensitive and specific indicators for double stranded DNA than the standard ethidium bromide dye when used in the instant method; YO-YO had the best performance. This dye's fluorescence is low in the absence of double stranded DNA and can increase about 3000-fold when bound to double-stranded DNA (23,24). This ultra sensitive nucleic acid stain, in combination with enzyme pretreatment, improved the signal ratio between positive and negative samples and allowed improved discrimination of HLA type.

EXAMPLE 3

Typing of clinical samples

The homogeneous detection method of the present invention was applied to detect PCR-SSP amplification in seven different and distinct clinical samples, and these samples were also typed by both standard serological assays and by PCR methods using agarose gel electrophoresis as the detection method. As shown in Table 3, the homogeneous detection method could distinguish the correct HLA-DR type for each specimen [positive fluorescence readings are noted in bold type]. However, the results of the analysis according to the present invention were obtained within about 30 minutes of completion of the PCR amplification. For most samples, the fluorescence was 5 to 20-fold greater in the positive PCR reaction than in the negative reactions.

In a subset of the reactions, significant

TABLE 3

HLA-DR typing using fluorescent homogeneous detection

| Primer pair | Sample 1 | Sample 2 | Sample 3 | Sample 4 | Sample 5 | Sample 6 | Sample 7 |
|---|---|---|---|---|---|---|---|
| DRBAMP-1 | 120 | 109 | 136 | <u>1524</u> | 432 | 109 | 114 |
| DRBAMP-2 | <u>3121</u> | 132 | 150 | 163 | 331 | <u>1926</u> | 176 |
| DRBAMP-15 | <u>2293</u> | 116 | 139 | 135 | 267 | <u>1943</u> | 114 |
| DRBAMP-16 | 101 | 111 | 213 | 134 | 451 | 114 | 165 |
| DRBAMP-3 | <u>2470</u> | 132 | 204 | 125 | 266 | 103 | 167 |
| DRBAMP-17 | <u>2881</u> | <u>2828</u>[a] | <u>3903</u>[a] | 267 | <u>3002</u>[a] | 179 | <u>1662</u>[a] |
| DRBAMP-18 | 142 | 156 | 121 | 164 | 689 | 143 | 195 |
| DRBAMP-4 | 705 | <u>4689</u> | 108 | <u>4608</u> | 1032 | 303 | 220 |
| DRBAMP-11 | 153 | 149 | 119 | 215 | <u>3146</u> | 142 | <u>1255</u> |
| DRBAMP-12 | 181 | 150 | <u>4003</u> | 219 | 817 | 567 | 173 |
| DRBAMP-7 | 220 | 199 | <u>4482</u> | 238 | <u>4031</u> | 242 | 185 |
| DRBAMP-8 | 236 | 165 | 248 | 426 | 823 | 150 | 151 |
| DRBAMP-9 | 269 | 588 | 262 | 263 | 271 | <u>1530</u> | 143 |
| DRBAMP-10 | 474 | 195 | 130 | 237 | 563 | 200 | 200 |
| DRBAMP-13A | 118 | <u>1994</u> | 150 | 132 | 400 | 109 | <u>1726</u> |
| DRBAMP-13B | 223 | 224 | 370 | 212 | 473 | 222 | 208 |
| DRBAMP-14A | 189 | 639 | 628 | 134 | 303 | 460 | 155 |
| DRBAMP-14B | 222 | 157 | 96 | 132 | 481 | 495 | 116 |
| DRBAMP-52 | <u>4841</u> | <u>2955</u> | <u>4521</u> | 206 | <u>4713</u> | 228 | <u>5057</u> |
| DRBAMP-53 | 171 | <u>4451</u> | <u>3795</u> | <u>4583</u> | <u>5153</u> | <u>1238</u> | 170 |
| HLA-DR type | DR15(2) | DR4 | DR7 | DR1 | DR7 | DR9 | DR11 |
| | DR17(3) | DR13 | DR12 | DR4 | DR11 | DR15(2) | DR13 |
| | DR52 | DR52 | DR52 | | DR52 | | DR52 |
| | | DR53 | DR53 | DR53 | DR53 | DR53 | |

[a]Cross amplification: DRBAMP-17 primer have cross amplification with DR11, DR12 and DR13.
(N) = The broad HLA-DR specificity.

background fluorescence was detectable. This background did not affect the accuracy of HLA typing in these specimens, and probably was the result of sub-optimal primer design and resulting primer-dimer formation and nonspecific amplification.

REFERENCES

1. Saiki R. K., Scharf S., Faloona F., Mullis K. B., Horn G. T., Erlich H. A., and Arnheim. (1985) Science 230, 1350–1354.
2. Saiki R. K., Gelfand D. H., Stoffel S., Scharf S. J., Higuchi R., Horn G. T., Mullis K. B., and Erlich H. A. (1988) Science 239, 487–489.
3. Maeda M., Murayama N., Ishii N., Uryu N., Ota M., Tsuji K., and Inoko H. (1989) Tissue Antigen 34, 290–298.
4. Uryu N., Maeda M., Ota M., Tsuji K., and Inoko H. (1990) Tissue Antigen 35, 20–31.
5. Angelini G., de Preval C., Gorski J., and Mach B. (1986) Proc. Natl. Acad. Sci. USA. 83, 4489–4493.
6. Bugawan T. L., Saiki R. K., Levenson C. H., Watson R. M., and Erlich H. A. (1988) Biotechnology 6, 943–947.
7. Tiercy J. M., Jeannet M., and Mach B. (1990) Blood Review 4, 9–15.
8. Eliaou J. F., Humbert M., Balaguer P., Gebuhrer L., Amsellem S., Betuel H., Nicolas J. C., and Clot J. (1989) Tissue Antigen 33, 475–485.
9. Schaf S. J., Grmith R. L., and Erlich H. A., (1991) Hum. Immunol. 30, 190–196.
10. Kawai S., Maekawajiri S., and Yamane A. (1993) Anal. Biochemistry 209, 6369.
11. Lazaro A. M., Fernandez-Vina M. A., Liu Z., and Stastny P. (1993) Hum. Immunol. 36, 243–248.
12. Nevinny-Stickel C. and Albert ED., (1993) Eur. J. Immunogenet. 20, 419427.
13. Saiki R. K., Walsh P. S., Levenson C. H., and Erlich H. A. (1989) Proc. Natl. Acad. Sci. USA. 86, 6230–6234.
14. Erlich H., Bugawan T., Begovich A. B., Scharf S., Griffith R., Saiki R., Higuchi R., and Walsh P. S. (1991) Eur. J. Immunogenet 18, 33–55.
15. Caillat-Zucman S., Garchon H-J., Constantino F., Cot S., and Bach J-F. (1993) Biotechniques 15, 526–531.
16. Fugger L., Morling N., Ryder L. P., Odum N., and Svejgaard A. (1990) J. Immunol Methgod. 129,175–185.
17. Olerup O., and Zetterquist H. (1991) Tissue Antigen 37, 197–204.
18. Olerup O., and Zetterquist H. (1992) Tissue Antigen 39, 225–235.
19. Ferencik S. and Grosse-Wilde H. (1993) Eur. J. Immunogenet. 20 123–125.
20. Chia D., Terasaki P., Chan H., Tonai R. and Siauw P.-A. (1993) Tissue Antigen 42 146–149.
21. Higuchi R., Dollinger G., Walsh P. S., and Griffith R. (1992) Bio/Technology 10, 413–417.
22. Higuchi R., Fockler C., Dollinger G., and Watson R. (1993) Bio/Techniques 11, 1026–1030.
23. Glazer A. N., and Rye H. S. (1992) Nature 359, 859–861.
24. Rye H. S., Dabora J. M., Quesada M. A., Mathies R. A., and Glazer A. N. (1993) Anal. Biochemistry 208, 144–150.
25. Yang S. Y., Milford E., Hammerling V., and Dupont B. (1987) in Immunobiology of HLA vol 1. Histocompatibility Testing. The B cell panel designated for the 10 th International Histocompatibility Workshop. pp 11–18 SpringerVerlag, N.Y.
26. Hopkins K. A., (1990) ASHI Laboratory Manual. Am. Soc. Histocompatibility Immunogenetics 195–201.
27. Little J. W., Lehman l. R. and Kaiser A. D. (1967) J. Biol. Chem. 242, 672.
28. Kwok S. Y., Mack D. H., Mullis K. B., Poiesz B. J., Ehrlich G. D., Blair D. and Friedman-Kein A. S. (1987) J Viol. 61,1690–1694.

I claim:

1. A method for detecting the presence of double-stranded, non-5'-phosphorylated DNA in a sample that may also contain 5'-phosphorylated DNA and single-stranded DNA, comprising:
   (a) adding to the sample an enzyme that specifically degrades single stranded DNA and an enzyme that specifically degrades DNA having 5'-phosphorylated ends, and incubating under conditions that permit the activity of said enzymes;
   (b) detecting the presence of DNA in the sample of step (a) wherein includes said DNA double stranded, non-5'-phosphorylated DNA.

2. A method for detecting the presence of one or more target DNA sequences in a sample containing 5'-phosphorylated DNA, comprising:
   (a) carrying out enzymatic amplification of one or more portions of the DNA in said sample to produce one or more amplification products wherein at least a portion of each of said amplification products is double stranded, non-5'-phosphorylated DNA;
   (b) adding an enzyme that specifically degrades single stranded DNA and an enzyme that specifically degrades DNA having 5'-phosphorylated ends, and incubating under conditions that permit the activity of said enzymes;
   (c) detecting the presence of DNA in the sample of step (b) wherein said DNA includes double stranded, non-5'-phosphorylated DNA.

3. The method of claim 2 wherein said 5'-phosphorylated DNA is biologically-derived.

4. The method of claim 2 wherein each of said steps are carried out in succession by addition of reagents to the reaction mixture resulting from the previous step, without any intervening purifications or separations.

5. The method of claim 2 wherein all steps are carried out in the same sample vessel.

6. The method of claim 5 wherein said sample vessel is a well of a microtiter plate.

7. The method of claim 2 wherein said detection of DNA is quantitative.

8. The method of claim 2 wherein said detection is qualitative, the presence or absence of amplified DNA in an unknown sample being determined by comparison with the results obtained using one or more known samples.

9. The method of claim 2 wherein said step of detecting the presence of DNA in the sample further comprises adding an intercalating fluorophore to said sample and detecting the fluorescence of the DNA when the resulting sample is excited by an appropriate excitation beam.

10. The method of claim 9 wherein said intercalating fluorophore is selected from the group of ethidium bromide (EtBr), ethidium homodimer (EthD), Thiazole yellow dimer (YO-YO), Thiazole orange dimer (TO-TO), and thiazole orange monomer (TO-PRO).

11. A method for detecting the presence of one or more target DNA sequences in a sample containing 5'-phosphorylated DNA, comprising:
    (a) carrying out primed enzymatic transcription on one or more portions of the DNA in said sample, using one or more primers that do not have 5'-phosphorylated ends;
    (b) adding to the DNA of said sample an enzyme that specifically degrades single stranded DNA, and incubating under conditions that permit the activity of said enzyme;
    (c) adding to the DNA remaining after step (b) an enzyme that specifically degrades DNA having 5'-phosphorylated ends, and incubating under conditions that permit the activity of said enzyme;
    (d) detecting the presence of DNA in the sample of step (c) wherein said DNA includes double stranded, non-5'-phosphorylated DNA.

12. A method for detecting the presence of one or more target DNA sequences in a sample containing 5'-phosphorylated DNA, comprising:
    (a) amplifying one or more portions of the DNA in said sample by polymerase chain reaction (PCR) to produce one or more double-stranded, non-5'-phosphorylated amplification products;
    (b) adding the enzymes lambda exonuclease and Exonuclease I and incubating under conditions that permit the activity of said enzymes;
    (c) adding an intercalating fluorophore selected from the group consisting of ethidium bromide (EtBr), ethidium homodimer (EthD), Thiazole yellow dimer (YO-YO), Thiazole orange dimer (TO-TO), and thiazole orange monomer (TO-PRO);
    (d) detecting the level of fluorescence emitted from the DNA in the sample of step (c) when illuminated with an appropriate excitation beam wherein said DNA includes double stranded, non-5'-phosphorylated DNA.

13. The method of claim 12 wherein said level of fluorescence is compared with the fluorescence levels observed when one or more known samples were analyzed by the method of claim 13.

14. The method of claim 12 wherein said PCR amplification is carried out using sequence specific primers.

15. The method of claim 14 wherein said sequence specific primers are specific for one or more human leukocyte antigens (HLAs).

16. A homogeneous method for detecting the presence or absence of one or more human leukocyte antigen (HLA) in a sample that is substantially of human biological origin, comprising:
    (a) using one or more HLA-sequence specific antigens in a polymerase chain reaction (PCR) to amplify one or more portions of the HLA-specific DNA in said sample;
    (b) adding the enzymes lambda exonuclease and Exonuclease I and incubating under conditions that permit the activity of said enzymes;
    (c) adding an intercalating fluorophore selected from the group of ethidium bromide (EtBr), ethidium homodimer (EthD), Thiazole yellow dimer (YO-YO), Thiazole orange dimer (TO-TO), and thiazole orange monomer (TO-PRO);
    (d) detecting the level of fluorescence emitted from the DNA in the sample of step (c) when illuminated with an appropriate excitation beam wherein said DNA includes double stranded, non-5'-phosphorylated DNA.

* * * * *

UNITED STATES PATENT AND TRADEMARK OFFICE
CERTIFICATE OF CORRECTION

PATENT NO. : 5,580,730
DATED : December 3, 1996
INVENTOR(S) : Naoaki OKAMOTO

It is certified that error appears in the above-indentified patent and that said Letters Patent is hereby corrected as shown below:

Column 1, line 66, after "presence of specific" insert --human leucocyte antigen-- and put "HLA" in parenthesis.

Column 6, line 29, change "Exonuclease 1" to --Exonuclease I--.

Column 7, line 20, change "Exonuclease 1" to --Exonuclease I--.

Column 7, line 44, change "Exonuclease 1" to --Exonuclease I--.

Column 7, line 56, change "Exonuclease 1" to --Exonuclease I--.

Column 15, Table 2, change "tratment" to --treatment--.

Column 15, line 43, change "Exonuclease 1" to --Exonuclease I--.

UNITED STATES PATENT AND TRADEMARK OFFICE
CERTIFICATE OF CORRECTION

PATENT NO. : 5,580,730
DATED : December 3, 1996
INVENTOR(S) : Naoaki OKAMOTO

It is certified that error appears in the above-indentified patent and that said Letters Patent is hereby corrected as shown below:

```
      Column 16, line 54, change "noted in bold type]" to
--underlined].--
```

Signed and Sealed this

Sixteenth Day of December, 1997

BRUCE LEHMAN

Attest:

Attesting Officer

Commissioner of Patents and Trademarks

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:1:

TTCTTGTGGC AGCTTAAGTT T                                                  21

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:2:

CCGCTGCACT GTGAAGCTCT                                                  20

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:3:

CCTGTGGCAG CCTAAGAGG                                                    19

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: HLA Class II DR allele primers ( x i ) SEQUENCE DESCRIPTION: SEQ ID NO:4:

CCGCTGCACT GTGAAGCTCT 20

( 2 ) INFORMATION FOR SEQ ID NO:5:

( i ) SEQUENCE CHARACTERISTICS:
                    ( A ) LENGTH: 19 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: HLA Class II DR allele primers ( x i ) SEQUENCE DESCRIPTION: SEQ ID NO:5:

CCTGTGGCAG CCTAAGAGG 19

( 2 ) INFORMATION FOR SEQ ID NO:6:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: HLA Class II DR allele primers ( x i ) SEQUENCE DESCRIPTION: SEQ ID NO:6:

TCCACCGCGG CCCGCGC 17

( 2 ) INFORMATION FOR SEQ ID NO:7:

( i ) SEQUENCE CHARACTERISTICS:
                    ( A ) LENGTH: 19 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                    ( A ) ORGANISM: HLA Class II DR allele primers ( x i ) SEQUENCE DESCRIPTION: SEQ ID NO:7:

CCTGTGGCAG CCTAAGAGG    19

( 2 ) INFORMATION FOR SEQ ID NO:8:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( A ) ORGANISM: HLA Class II DR allele primers ( x i ) SEQUENCE DESCRIPTION: SEQ ID NO:8:

ACCGCGGCGC GCCTGTCT    18

( 2 ) INFORMATION FOR SEQ ID NO:9:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( A ) ORGANISM: HLA Class II DR allele primers ( x i ) SEQUENCE DESCRIPTION: SEQ ID NO:9:

CACGTTTCTT GGAGTACTCT AC    22

( 2 ) INFORMATION FOR SEQ ID NO:10:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( A ) ORGANISM: HLA Class II DR allele primers ( x i ) SEQUENCE DESCRIPTION: SEQ ID NO:10:

GCAGTAGTTG TCCACCCGGC    20

( 2 ) INFORMATION FOR SEQ ID NO:11:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: HLA Class II DR allele primers ( x i ) SEQUENCE DESCRIPTION: SEQ ID NO:11:

CACGTTTCTT GGAGTACTCT AC      22

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:12:

AGCTCCGTCA CCGCCCGGA      19

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:13:

CACGTTTCTT GGAGTACTCT AC      22

( 2 ) INFORMATION FOR SEQ ID NO:14:

( i ) SEQUENCE CMMCTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:14:

CTCCTGGTTA TGGAAGTATC TC      22

( 2 ) INFORMATION FOR SEQ ID NO:15:

( i ) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: HLA Class II DR allele primers (xi) SEQUENCE DESCRIPTION: SEQ ID NO:15:

GTTTCTTGGA GCAGGTTAAA 20

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: HLA Class II DR allele primers (xi) SEQUENCE DESCRIPTION: SEQ ID NO:16:

CCGCTGCACT GTGAAGCTCT 20

(2) INFORMATION FOR SEQ ID NO:17:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: HLA Class II DR allele primers (xi) SEQUENCE DESCRIPTION: SEQ ID NO:17:

CACGTTTCTT GGAGTACTCT AC 22

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: HLA Class II DR allele primers ( x i ) SEQUENCE DESCRIPTION: SEQ ID NO:18:

CTGGCTGTTC CAGTACTCCT 20

( 2 ) INFORMATION FOR SEQ ID NO:19:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOLTRCE:
        ( A ) ORGANISM: HLA Class II DR allele primers ( x i ) SEQUENCE DESCRIPTION: SEQ ID NO:19:

CACGTTTCTT GGAGTACTCT AC 22

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:20:

GCTGTTCCAG GACTCGGCGA 20

( 2 ) INFORMATION FOR SEQ ID NO:21:

( i ) SEQUENCE CMMCTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:21:

CCTGTGGCAG GGTAAGTATA 20

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: HIA Class II DR allele primers ( x i ) SEQUENCE DESCRIPTION: SEQ ID NO:22:

CCCGTAGTTG TGTCTGCACA C            21

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:23:

GTACTCTACG GGTGAGTGTT            20

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNFSS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:24:

CTGCAGTAGG TGTCCACCAG            20

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:25:

CGGAGCGGGT GCGGTAT            17

( 2 ) INFORMATION FOR SEQ ID NO:26:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: HLA Class II DR allele primers ( x i ) SEQUENCE DESCRIPTION: SEQ ID NO:26:

CCCGTAGTTG TGTCTGCACA C                    21

( 2 ) INFORMATION FOR SEQ ID NO:27:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE,
    ( A ) ORGANISM: HLA Class II DR allele primers ( x i ) SEQUENCE DESCRIPTION: SEQ ID NO:27:

CGGTTGCTGG AAAGACGCG                       19

( 2 ) INFORMATION FOR SEQ ID NO:28:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: HLA Class II DR allele primers ( x i ) SEQUENCE DESCRIPTION: SEQ ID NO:28:

CCGCTGCACT GTGAAGCTCT                      20

( 2 ) INFORMATION FOR SEQ ID NO:29:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

( A ) ORGANISM: HLA Class II DR allele primers ( x i ) SEQUENCE DESCRIPTION: SEQ ID NO:29:

CACGTTTCTT GGAGTACTCT AC          22

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:30:

GTCCACCGCG GCCCGCTC          18

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:31:

CACGTTTCTT GGAGTACTCT AC          2

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORCANism: HLA Class II DR allele primers ( x i ) SEQUENCE DESCRIPTION: SEQ ID NO:32:

CTGTTCCAGT ACTCGGCGCT          20

( 2 ) INFORMATION FOR SEQ ID NO:33:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: HLA Class II DR allele primers ( x i ) SEQUENCE DESCRIPTION: SEQ ID NO:33:

CACGTTTCTT GGAGTACTCT AC      22

( 2 ) INFORMATION FOR SEQ ID NO:34:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:34:

CCACCTCGGC CCGCCTCC      18

( 2 ) INFORMATION FOR SEQ ID NO:35:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:35:

CACGTTTCTT GGAGTACTCT AC      22

( 2 ) INFORMATION FOR SEQ ID NO:36:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:36:

CACCGCGGCC CGCCTCTG      18

( 2 ) INFORMATION FOR SEQ ID NO:37:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE-DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:37:

CCCCAGCACG TTTCTTGGAG CT        22

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:38:

CCGCTGCACT GTGAAGCTCT        20

( 2 ) INFORMATION FOR SEQ ID NO:39:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: HLA Class II DR allele primers ( x i ) SEQUENCE DESCRIPTION: SEQ ID NO:39:

AGCGAGTGTG GAACCTGAT        19

( 2 ) INFORMATION FOR SEQ ID NO:40:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: HLA Class II DR allele primers (xi) SEQUENCE DESCRIPTION: SEQ ID NO:40:

CTCCACAACC CCGTAGTTGT A                                                                                         2 1